US011259131B2

(12) United States Patent
West et al.

(10) Patent No.: US 11,259,131 B2
(45) Date of Patent: Feb. 22, 2022

(54) HEARING AID IMPLANT RECHARGING SYSTEM

(71) Applicant: NANOEAR CORPORATION, INC., Houston, TX (US)

(72) Inventors: William Clark West, South Pasadena, CA (US); Michael M. Moore, Surfside, FL (US); Ron L. Moses, Bellaire, TX (US); Smruti Mirchandani, Houston, TX (US)

(73) Assignee: NANOEAR CORPORATION, INC., Houston, TX (US)

(*) Notice: Subject to any disclaimer, the term of this patent is extended or adjusted under 35 U.S.C. 154(b) by 70 days.

(21) Appl. No.: 16/893,787

(22) Filed: Jun. 5, 2020

(65) Prior Publication Data

US 2020/0389742 A1 Dec. 10, 2020

Related U.S. Application Data

(60) Provisional application No. 62/858,216, filed on Jun. 6, 2019.

(51) Int. Cl.
*H04R 25/00* (2006.01)
*H02S 40/38* (2014.01)
*H01L 31/042* (2014.01)

(52) U.S. Cl.
CPC ......... *H04R 25/602* (2013.01); *H01L 31/042* (2013.01); *H02S 40/38* (2014.12);
(Continued)

(58) Field of Classification Search
CPC ............ H04R 2225/31; H04R 2225/67; H04R 25/554; H04R 25/602; H04R 1/1025
(Continued)

(56) References Cited

U.S. PATENT DOCUMENTS 5,176,620 A 1/1993 Gilman
5,220,918 A 6/1993 Heide et al.
(Continued)

FOREIGN PATENT DOCUMENTS

CN 104799971 A 7/2015
JP 2005516505 A * 6/2005
(Continued)

OTHER PUBLICATIONS

International Search Report and Written Opinion dated Jan. 20, 2020 for Application No. PCT/US2019/054750.
(Continued)

*Primary Examiner* — Phylesha Dabney
(74) *Attorney, Agent, or Firm* — Patterson & Sheridan, LLP

(57) ABSTRACT

The present disclosure relates to charging and recharging systems for compact hearing aids, components thereof, and support devices therefor. The charging and recharging systems generally include a light emitting device, such as an aural insert having a light emitting diode, and a photovoltaic cell disposed on an implanted hearing aid. In operation, the light emitting device is positioned in or near the entrance of the ear canal and transmits light energy across the ear canal towards the implanted hearing aid. The photovoltaic cell receives the light energy and converts the light energy into stored electricity to power the hearing aid.

20 Claims, 18 Drawing Sheets

(52) U.S. Cl.
CPC ....... *H04R 25/554* (2013.01); *H04R 2225/31* (2013.01); *H04R 2225/67* (2013.01)

(58) Field of Classification Search
USPC .......................................................... 381/312
See application file for complete search history.

(56) References Cited

U.S. PATENT DOCUMENTS

| | | | |
|---|---|---|---|
| 5,338,287 | A | 8/1994 | Miller et al. |
| 6,084,975 | A | 7/2000 | Perkins |
| 6,137,889 | A | 10/2000 | Shennib et al. |
| 6,387,039 | B1 | 5/2002 | Moses |
| 7,003,353 | B1 * | 2/2006 | Parkhouse ........... A61N 1/3787 |
| | | | 607/45 |
| 7,748,493 | B2 | 7/2010 | Moses et al. |
| 7,983,435 | B2 | 7/2011 | Moses |
| 8,433,083 | B2 | 4/2013 | Abolfathi et al. |
| 8,630,712 | B2 | 1/2014 | Moses et al. |
| 9,544,675 | B2 * | 1/2017 | Facteau ................. G02C 11/06 |
| 9,597,522 | B2 | 3/2017 | Meskens |
| 2003/0065245 | A1 | 4/2003 | Easter et al. |
| 2005/0152146 | A1 | 7/2005 | Owen et al. |
| 2007/0154030 | A1 | 7/2007 | Moses |
| 2009/0149922 | A1 | 6/2009 | White |
| 2010/0034409 | A1 * | 2/2010 | Fay ...................... H04R 23/008 |
| | | | 381/326 |
| 2010/0312040 | A1 * | 12/2010 | Puria ................... H04R 25/606 |
| | | | 600/25 |
| 2015/0382117 | A1 | 12/2015 | Vermeiren |
| 2016/0100263 | A1 | 4/2016 | Huettenbrink |
| 2017/0071509 | A1 | 3/2017 | Pandey et al. |
| 2018/0270560 | A1 | 9/2018 | Perkins et al. |
| 2019/0327567 | A1 | 10/2019 | Blum et al. |

FOREIGN PATENT DOCUMENTS

| | | |
|---|---|---|
| KR | 20050039445 A | 4/2005 |
| KR | 20070093049 A | 9/2007 |
| KR | 20100005940 A | 1/2010 |
| WO | 2010133704 A2 | 11/2010 |
| WO | 16/205373 A1 | 12/2016 |

OTHER PUBLICATIONS

International Search Report and Written Opinion dated Jan. 31, 2020 for Application No. PCT/US2019/054739.

PCT International Search Report and Written Opinion dated Sep. 2, 2020, for International Application No. PCT/US2020/036286.

* cited by examiner

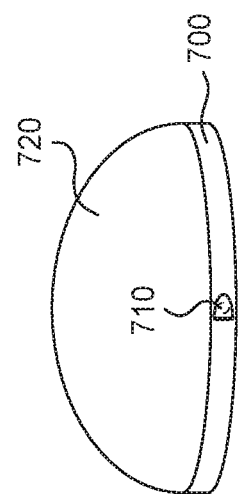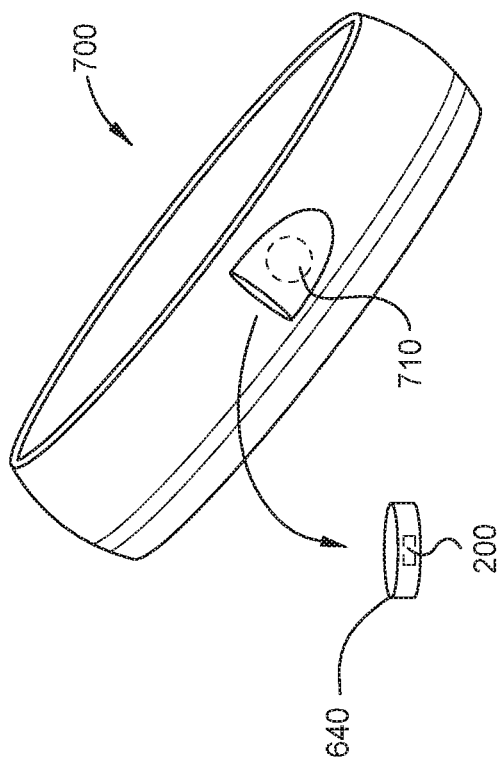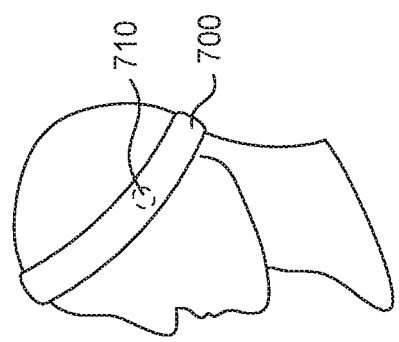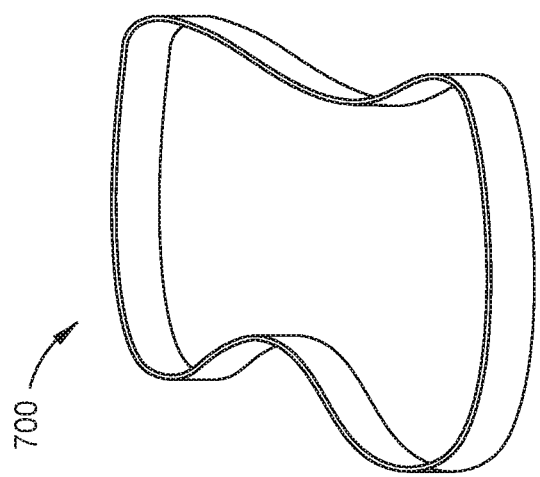

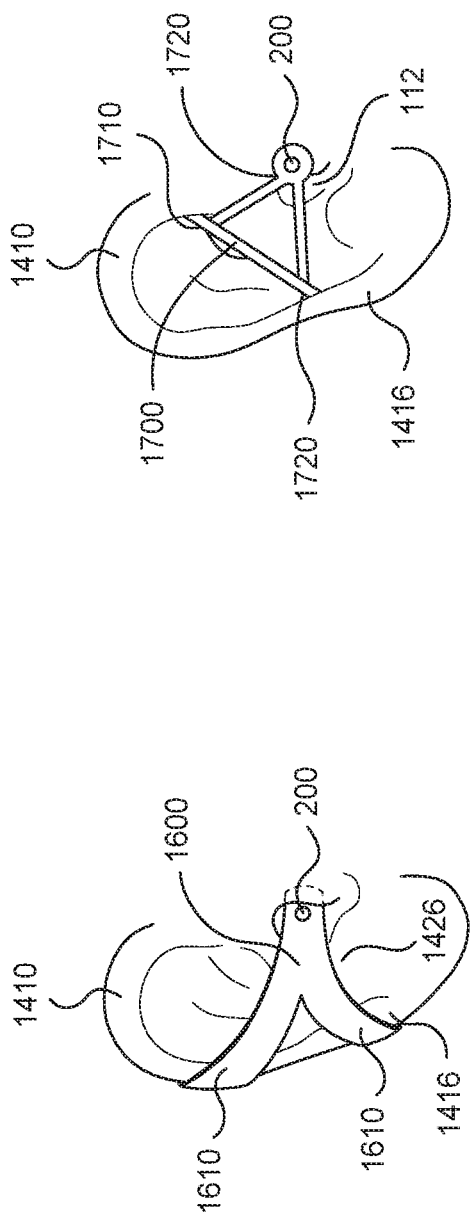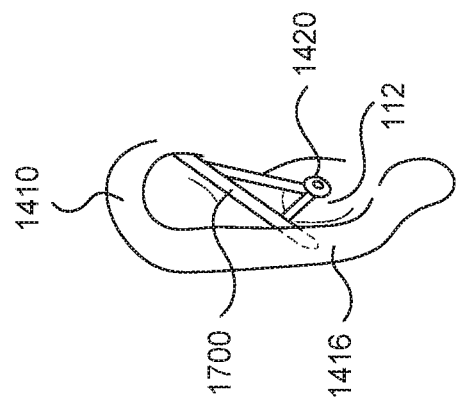

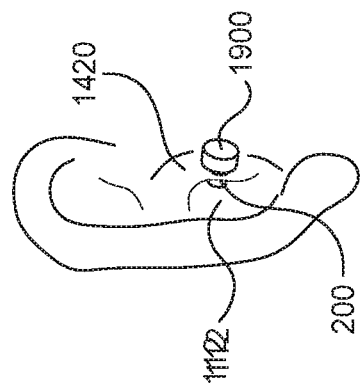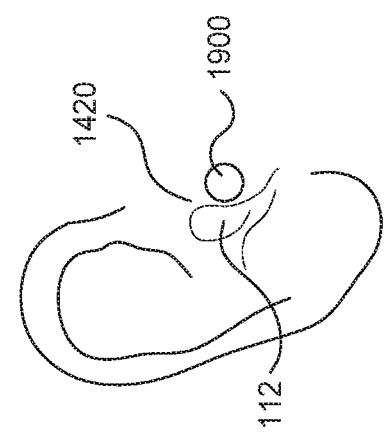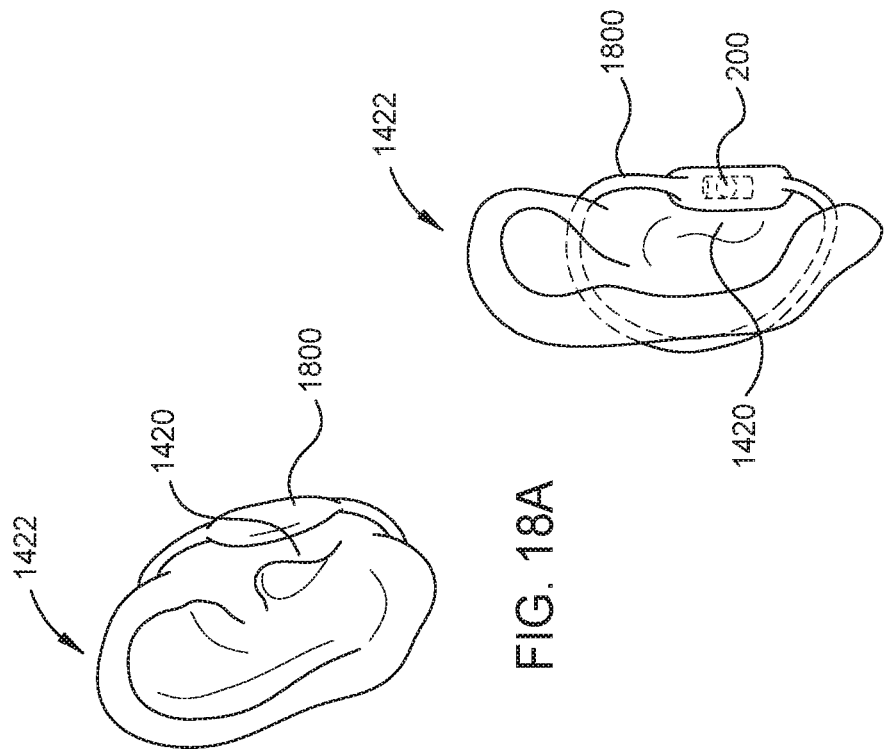

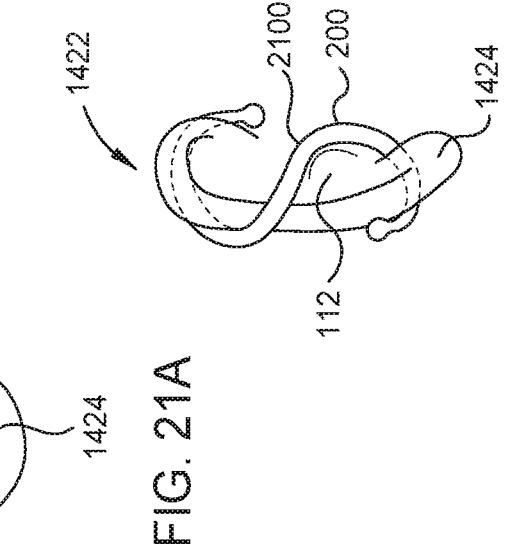
FIG. 21A
FIG. 21B
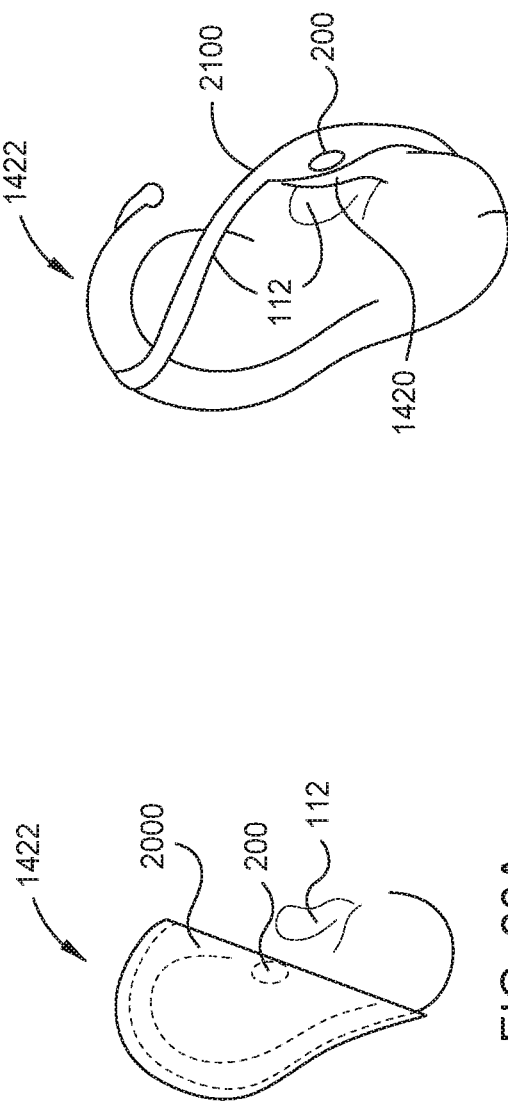
FIG. 20A
FIG. 20B

HEARING AID IMPLANT RECHARGING SYSTEM

CROSS-REFERENCE TO RELATED APPLICATIONS

This application claims benefit of U.S. Provisional Patent Application Ser. No. 62/858,216, filed on Jun. 6, 2019, which is herein incorporated by reference in its entirety.

BACKGROUND

Field

Embodiments of the present disclosure generally relate to assistive hearing devices and methods for recharging thereof. More particularly, embodiments of the present disclosure are related to recharging of hearing aid implants via light emitting diode-photovoltaic systems.

Description of the Related Art

Hearing aids are well known and typically include a microphone, an amplifier, and a speaker. Typically, the microphone receives a sound wave and converts the wave into an electrical signal, the amplifier amplifies the electrical signal, and the speaker converts the amplified signal into amplified sound waves that impart vibrations to the tympanic membrane or ear drum in the ear. Traditionally, hearing aids are mounted outside the ear canal, particularly around the outer ear. The externally mounted hearing aid has the advantage of accessibility to adjust the volume of sound and change batteries. However, many users find such externally mounted hearing aids to be relatively bulky and objectionable for cosmetic and comfort reasons.

An alternative to externally mounted hearing aids are internally mounted hearing aids disposed in an ear canal of a user. Conventional internally mounted hearing aids offer better cosmetic appearance, but have disadvantages as well. Such hearings aids are usually employed for extended periods of time and utilize microelectronic chipsets that consume large amounts of power, therefore requiring repeated replacement of batteries every few days or frequent recharging with bulky inductive charging devices. The frequent battery replacement and/or recharging requirements make internally mounted hearing aids less desirable for active people and children, resulting in a significant impact on quality life for the hearing impaired members of the population.

Therefore, what is needed in the art are improved methods and apparatus for recharging internally mounted hearing aids.

SUMMARY

The present disclosure generally relates to methods and apparatus for recharging of internally mounted hearing aids, and more particularly, recharging of internally mounted hearing aid implants via light emitting diode-photovoltaic systems.

In one embodiment, a charging system for a hearing aid implant disposed through a tympanic membrane of an ear includes one or more photovoltaic (PV) cells located on a proximal end of the hearing aid implant and one or more light sources configured to be inserted in or near an entrance of an ear canal of the ear. During operation, the one or more light sources emit a light energy receivable by the one or more PV cells to charge the hearing aid implant.

In one embodiment, a charging system for a hearing aid implant disposed through a tympanic membrane of an ear includes one or more photovoltaic (PV) cells located on a proximal end of the hearing aid implant and a charging device configured to be inserted in or near an entrance of an ear canal of the ear. The charging device further includes one or more light sources emitting a light energy receivable by the one or more PV cells of the hearing aid implant and having a wavelength corresponding to a wavelength range of high reflectivity by one or more surfaces of the ear canal. During operation, the one or more PV cells convert the light energy into stored electricity to power the hearing aid implant In one embodiment, a charging system for a hearing aid implant disposed through a tympanic membrane of an ear includes one or more photovoltaic (PV) cells located on a proximal end of the hearing aid implant and a charging device configured to be inserted in or near an entrance of an ear canal of the ear. The charging device further includes one or more high spectral purity, high efficiency resonant cavity light emitting diodes (LEDs) for emitting a light energy having a wavelength corresponding to a wavelength range of high reflectivity by one or more surfaces of the ear canal. A support device is coupled to the one or more LEDs and is configured to at least partially rest external to the ear canal and secure the charging device to the ear. During operation, the one or more PV cells are configured to absorb the light energy emitted directly from the one or more LEDs as well as light energy reflected by the one or more surfaces of the ear canal and convert the light energy into stored electricity to power the implanted hearing aid.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIGS. 7A-7D illustrate an external support device for the wireless charging device of FIG. 1.

FIGS. 16A-16B illustrate an external support device for the wireless charging device of FIG. 1.

FIGS. 17A-17B illustrate an external support device for the wireless charging device of FIG. 1.

FIGS. 18A-18B illustrate an external support device for the wireless charging device of FIG. 1.

FIGS. 19A-19B illustrate an external support device for the wireless charging device of FIG. 1.

FIGS. 20A-20B illustrate an external support device for the wireless charging device of FIG. 1.

FIGS. 21A-21B illustrate an external support device for the wireless charging device of FIG. 1.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure relates to charging and recharging systems for compact hearing aids, components thereof, and support devices therefor. The charging and recharging systems generally include a light emitting device, such as an aural insert having a light emitting diode, and a photovoltaic cell disposed on an implanted hearing aid. In operation, the light emitting device is positioned in or near the entrance of the ear canal and transmits light energy across the ear canal towards the implanted hearing aid. The photovoltaic cell receives the light energy and converts the light energy into stored electricity to power the implanted hearing aid. In certain embodiments, the light emitting device further transmits one or more wireless command signals to the implanted hearing aid, which may execute commands (e.g., functions) based on the wireless command signals received from the light emitting device.

The embodiments described herein provide exemplary configurations of implanted hearing aids contemplated by the present disclosure. However, any other suitable configurations for hearing aids that modulate the velocity or the position of the tympanic membrane, by direct or indirect modulation, are also contemplated. The embodiments that follow discuss inserting the disclosed compact hearing aids through the tympanic membrane as an example; however, the compact hearing aids are also disposable in other locations within the ear.

Anatomy of the Ear

Figure 1:
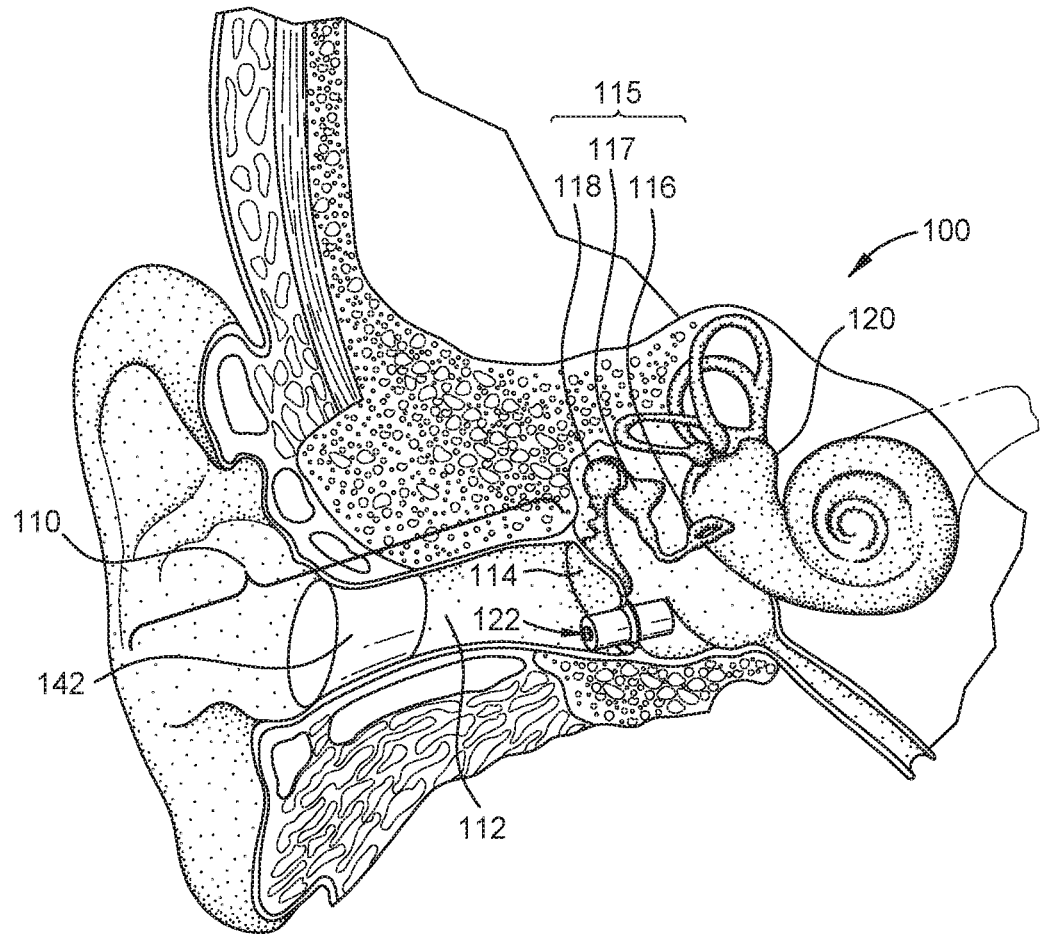
FIG. 1 illustrates a schematic cross-sectional view of an ear having a hearing aid implanted through a tympanic membrane and a wireless charging device inserted near an entrance of the ear canal.

FIG. 1 is a schematic cross-sectional view of an ear 100 having a hearing aid implanted through the tympanic membrane and a wireless charging device inserted into the ear canal thereof. The ear 100 includes an outer ear 110, an ear canal 112 coupled to the outer ear 110, and a tympanic membrane 114 disposed near a proximal end of the ear canal 112 from the outer ear 110. The structure of the outer ear 110 provides a "funnel" to direct and amplify the amplitude of sound waves into the ear canal 112. An ossicular chain 115, located in a middle ear and disposed on a medial side of the tympanic membrane 114 from the outer ear 110, couples and amplifies vibrations from the tympanic membrane 114 to an inner ear having a spiral structure known as the cochlea 120. The cochlea 120 converts the vibrations into impulses to the brain.

Hearing aids, such as hearing aid 122, of the present disclosure can be inserted through the outer ear 110 into the ear canal 112 and at least partially through the tympanic membrane 114. The hearing aid 122 generally includes a sensor, such as a microphone, and at least one eardrum stimulating member described in more detail below. The hearing aid 122 generally receives sound waves conducted from the outer ear 110 through the ear canal 112, converts the sound waves into electrical or electromagnetic signals, and converts the electrical signals into mechanical motion, which is typically called a feed-forward system. The mechanical motion is used to impact the tympanic membrane 114, and/or portions of the middle and inner ear, to vibrate the ossicular chain 115, specifically the malleus 118, the incus 117, and the stapes 116. These three bones in the ossicular chain 115 act as a set of levers that amplify the amplitude of the vibrations received by the tympanic membrane 114. The stapes 116 is coupled to the entrance of a spiral structure known as the cochlea 120 that contains an inner ear fluid. The mechanical vibrations of stapes 116 cause the fluid to develop fluid impulses that cause small hair-like cells (not shown) in the cochlea 120 to vibrate. The vibrations are transformed into electrical impulses, which are transmitted to neuro-pathways in the hearing center of the brain resulting in the perception of sound.

Because the hearing aid 122 may be fixedly inserted through the tympanic membrane 114, one or more energy sources (e.g., batteries) thereof may be recharged with a wireless charging device 142. The charging device 142, like the hearing aid 122, may also be inserted through the outer ear 110 and into the ear canal 112 for wireless transfer of energy to the hearing aid 122 implanted therein to power the hearing aid 122. Additionally, the charging device 142 may wirelessly communicate with the hearing aid 122 and transfer one or more wireless command signals thereto. In certain embodiments, the hearing aid 122 audibly signals to the user a power level (e.g., charge state) thereof and/or the execution of the one or more commands communicated by the wireless charging device 142. For example, the hearing aid 122 may produce an audible tone for the user signaling a low-charge level, a fully-charged level, a volume level and/or adjustment, and activation and/or deactivation (e.g., power on or power off) of the hearing aid 122.

As described in more detail below, the charging device 142 generally includes one or more light emitting components (e.g., light sources) for optically coupling with the hearing aid 122 to transfer energy thereto in the form of light. Accordingly, the hearing aid 122 generally includes one or more photovoltaic (PV) assemblies (e.g., light-receiving surfaces or cells) for receiving light emitted from the charging device 142 and converting the light into electricity using semiconducting materials exhibiting the photovoltaic effect.

Light Emitting Systems and Devices

Figure 2A:
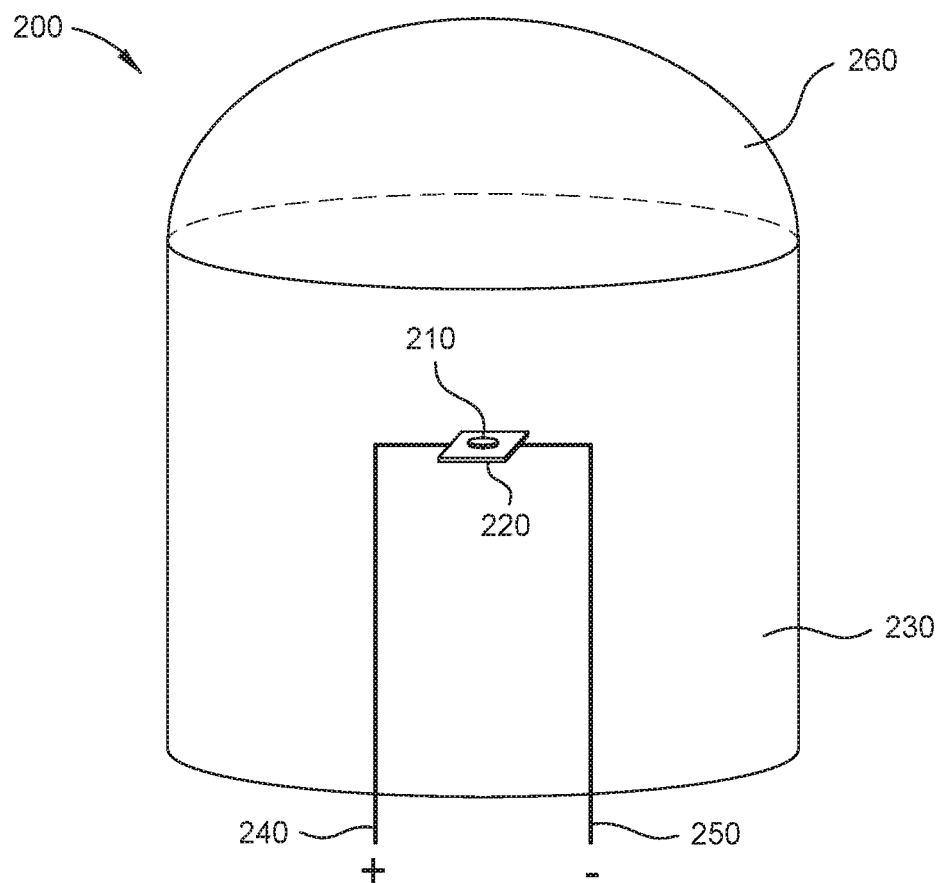
FIGS. 2A-2B illustrate schematic cross-sectional views of a light source assembly of the wireless charging device of FIG. 1.
Figure 2B:
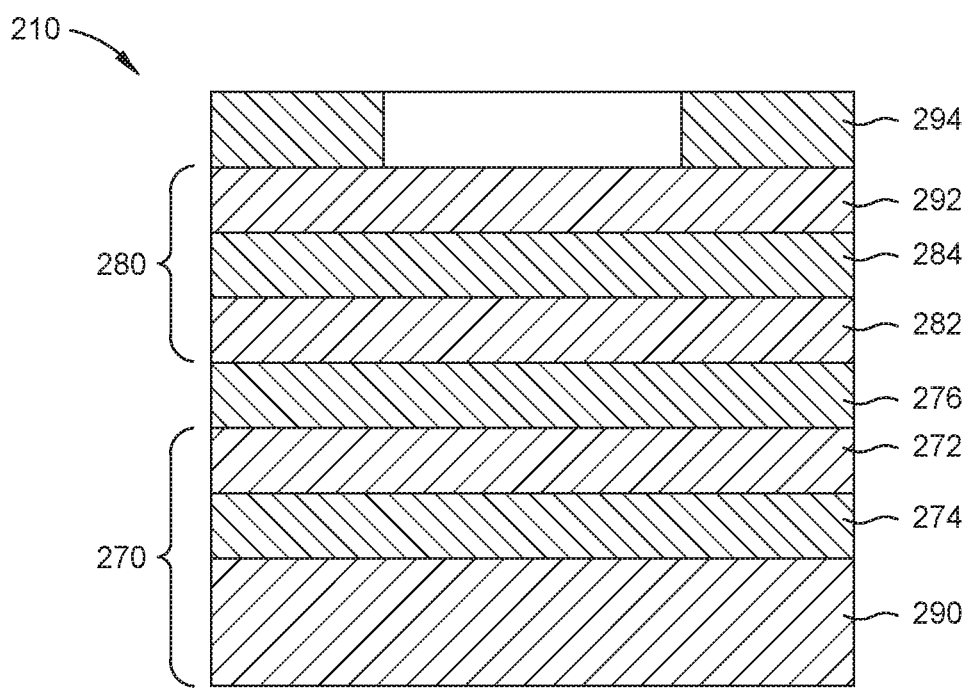

FIGS. 2A-2B illustrate schematic cross-sectional views of a light source assembly 200 and a light source 210 of the wireless charging device 142, respectively. The light source assembly 200 is generally disposed on a distal end of the charging device 142, which may include an earpiece or aural insert that is configured to be easily inserted into and removed from the ear canal. The ability to insert and remove the charging device 142 from the ear canal enables charging/recharging of the charging device 142 itself and/or cleaning thereof. During operation, the light source assembly 200 may be disposed at a distance of about 30 cm or less from a light receiver, such as a photovoltaic cell, of the hearing aid 122. For example, upon insertion of the charging device 142 into or near the ear canal, the light source assembly 200 may be disposed at a distance of between about 2 mm and about 30 mm from the hearing aid 122, such as a distance of between about 10 mm and about 20 mm from the hearing aid 122. In certain embodiments, the light source assembly 200 is disposed at a distance from the hearing aid 122 substantially equal to a length of the user's ear canal. As used herein, the term "distal" refers to a portion of the light emitting assemblies, hearing aids, or support devices closest to the cochlea when inserted into the ear canal, or a direction toward the cochlea. The term "proximal" refers to a portion of the light emitting assemblies or hearing aids furthest to the cochlea when inserted into the ear canal, or a direction away from the cochlea.

As depicted in FIG. 2A, the light source assembly 200 includes at least one light source 210 disposed on a light-reflective substrate holder 220 and encapsulated within an encapsulant 230. In certain embodiments, a plurality of light sources 210 are arranged in one or more arrays on the light-reflective substrate holder 220 and are encapsulated within the encapsulant 230. During operation, the substrate holder 220 reflects any radially- and/or proximally-emitted light from the light sources 210 in a distal direction through the encapsulant 230, thus enabling maximum light delivery to the hearing aid 122 within the ear canal. Accordingly, the substrate holder 220 may be formed of thin reflective films of aluminum, silver, chromium, and other suitable metals having a cup-like morphology around each light source 210. In certain embodiments, the substrate holder 220 is formed of multiple layers of materials with differing optical properties, such as titanium dioxide and silicon dioxide, to form a Bragg mirror structure. The encapsulant 230 is formed of any suitable optically-clear materials including, but not limited to, epoxy and polyurethane resins, for protecting the light source 210 while also enabling transmission of light therefrom. The light source assembly 200 further includes two terminals 240 and 250 disposed through the encapsulant 230 and electrically coupled with the at least one light source 210. The terminals 240 and 250 are positive and negative current-driving terminals, respectively, that enable application of current to the light sources 210 to turn the light sources 210 on.

In certain embodiments, the light source assembly 200 also includes one or more secondary optics, such as a lens 260, to manipulate light emission distribution of the light sources 210. Generally, the lens 260 focuses or collimates light from the one or more light sources 210 in the distal direction to improve light delivery to the hearing aid 122. In certain embodiments, the lens 260 creates a light field having a diameter of approximately 1 cm or greater to illuminate the entire ear canal, thus ensuring that the hearing aid 122 is within a propagation path of the light source assembly 200. In certain embodiments, the lens 260 is configured to focus the emitted light on a focal plane disposed at a distance from the light source assembly 200 between about 1 mm and about 30 mm, such as between about 5 mm and about 25 mm, such as between about 10 mm and about 20 mm, such as about 15 mm. To accommodate for patient-to-patient variation of ear canal length, the light-propagating properties of the lens 260 may be adjustable.

Each light source 210 generally emits incoherent light having a wavelength corresponding to the wavelength range of high light reflectivity by the tympanic membrane and other surfaces within the ear canal, thus enabling multiple reflections and optimal capture of indirect scattered light by the hearing aid 122. For example, the light sources 210 may include light emitting diodes (LED) configured to emit light having a wavelength in the range from about 400 nm to about 1100 nm, such as a wavelength in the range from about 400 nm to about 870 nm, such as a wavelength of about 800 nm. In certain embodiments, the light sources 210 include narrow wavelength light sources, such as a $Ga_xAl_{(1-x)}As$-type LEDs, where x is between about 0.5 and about 1. In certain other embodiments, the light sources 210 include multiple wavelength light sources, such as a white light LEDs. It is further contemplated that a peak wavelength of the light sources 210 is generally between about 25 nm and 75 nm less than a peak absorptivity of receiving PV cells of the hearing aid 122. For example, the peak wavelength of the light sources 210 may be about 50 nm less than a peak absorptivity of the PV cells of the hearing aid 122.

Although described above as being LEDs, the light sources 210 of the light source assembly 200 may include any suitable types of light sources for illuminating the PV assembly of the hearing aid 122 while also having a low power density to avoid uncomfortable heating of the patient's ear canal. For example, the light sources may have a maximum power dissipation of about 120 mW or less. Other suitable types of light sources include incandescent light and coherent light sources, such as laser-based light sources.

An exemplary structure of an LED-type light source 210 is depicted in FIG. 2B. The light source 210 depicted in FIG. 2B is a high spectral purity, high efficiency resonant cavity LED (RCLED) and comprises an active region 276 disposed between a plurality of n-type semiconductor layers 270 and a plurality of p-type semiconductor layers 280, thus forming a double heterostructure. The heterostructure of the LED-type light source 210 is stacked between an n+(very heavily doped n-type) substrate 290 and a p+ GaAs layer 292 adjacent a metal contact 294 for coupling with terminals 240, 250. In certain embodiments, the active region 276 includes one or more multiquantum well layers formed of GaInP, AlGaAs, and/or $Al_{(1-x)}Ga_xInP$ to trap injected charge carriers therein and improve recombination of electrons and holes for photon emission. To improve confinement of charge carriers within the active region 276, the pluralities of layers 270, 280 may include one or more cladding layers 272, 282 adjacent to the active region 276 and formed of GaAs. In certain embodiments, the pluralities of layers 270, 280 may further include one or more Bragg reflector layers 274, 284 to increase the light output power of the light source 210. Although not depicted, it is further contemplated that the light source 210 may also be a surface mounted device LED (SMD LED) having an LED chip with a phosphor layer disposed in a flat top lens mounted on a printed circuit board (PCB). Furthermore, although exemplary embodiments of the light source 210 are described with reference to FIG. 2B, those skilled in the art will understand that the light source 210 may be optimized by tailoring the composition and structure of the various components and/or layers thereof.

Photovoltaic Systems and Devices

Figure 3A:
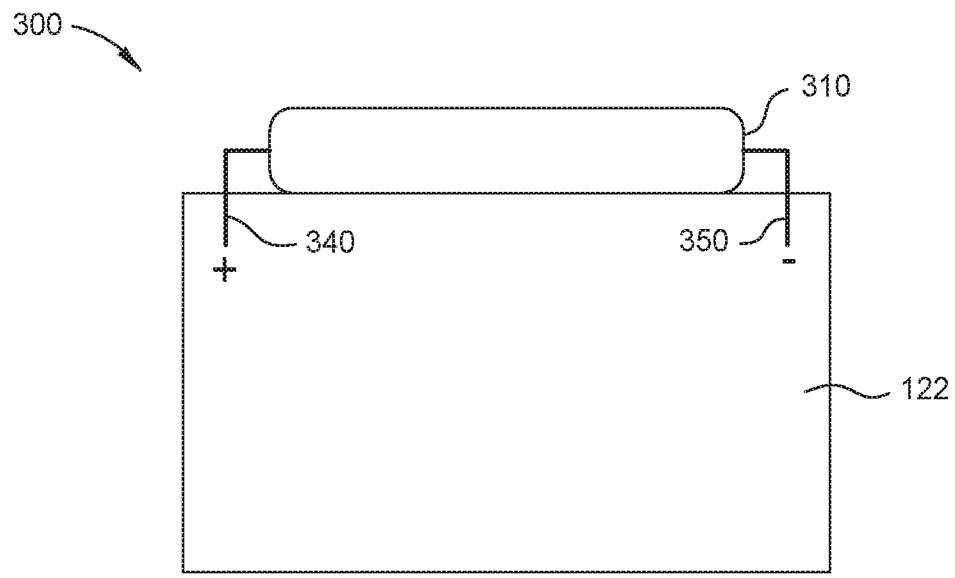
FIGS. 3A-3B illustrate schematic cross-sectional views of a photovoltaic assembly of the hearing aid of FIG. 1.
Figure 3B:
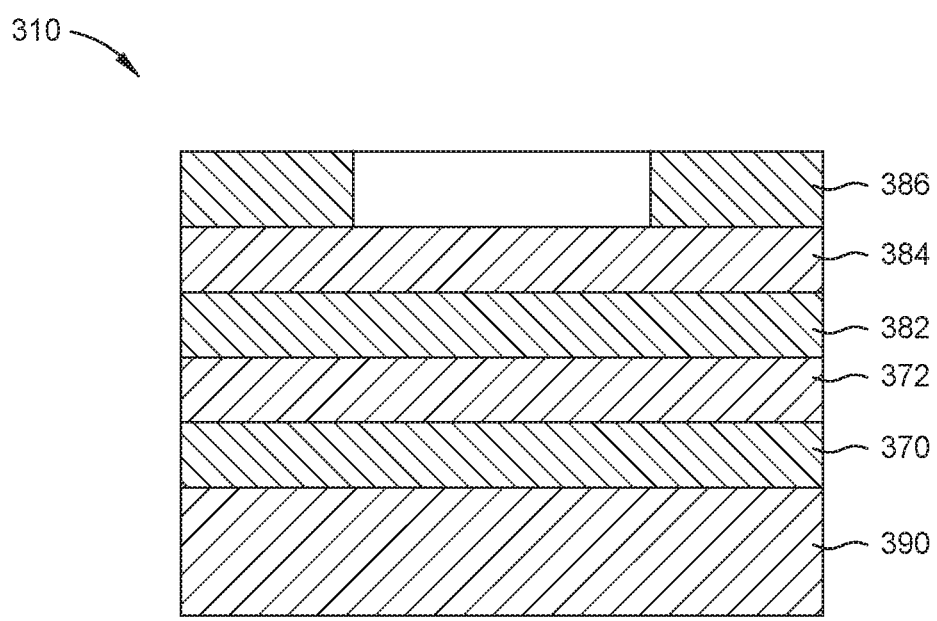

FIGS. 3A-3B illustrate schematic cross-sectional views of a photovoltaic (PV) assembly 300 and a PV cell 310 of the hearing aid 122, respectively. The PV assembly 300 is generally disposed on a proximal portion of the hearing aid 122 within the ear canal for optical coupling with the charging device 142 while avoiding interference with the sound detection and amplification functions of the hearing aid 122. As depicted in FIG. 3A, the PV assembly generally includes at least one PV cell 310 that electrically couples with a power input of the hearing aid 122 via positive and negative leads 340 and 350, respectively. In certain embodiments, the PV assembly 300 includes a plurality of PV cells 310 arranged in one or more arrays. For example, a plurality of PV cells 310 may be partitioned and isolated such that they can be connected in a serial configuration for higher voltage output, thus eliminating the need for DC-DC converters and eliminating related DC-DC up-conversion losses.

Generally, each PV cell 310 is a single or multi-junction (e.g., double junction, triple junction) semiconductor device configured to absorb the energy of light produced by the charging device 142 and convert it directly into electricity to power the hearing aid 122. Utilization of multiple junctions may increase the energy absorption and/or conversion properties of the PV cells 310. In certain embodiments, the output voltage of a single junction GaAs PV is between about 0.2V and about 0.9V, and the output power is between about 10 mW and about 80 mW, depending on current density. The PV cells 310 may be optimized for absorption of either broad or narrow wavelength light, such as achromatic or monochromatic light. In certain embodiments, the PV cells 310 absorb light energy emitted by the charging device 142 that is reflected off the skin within the ear canal. For example, the light sources 210 and the PV cells 310 may emit and absorb light having a wavelength corresponding to optimal skin reflectivity, such as about 800 nm. At 800 nm, surfaces within the ear canal, such as those of the tympanic membrane, have a high reflectance (0.8), low absorbance (0.1), and low transmittance (0.1), thus enabling optimum transmission of light energy within the ear canal.

An exemplary structure of a PV cell 310 is depicted in FIG. 3B according to embodiments of this disclosure. As shown, the PV cell 310 is a GaAs-based PV cell formed on a thinned N+ GaAs substrate 390, thus having a reduced mass and profile. An n-type Bragg reflector layer 370, an n-type base layer 372, a thin p-type emitter layer 382, and a p-type window layer 384 are stacked above the substrate 390. Like the substrate 390, the base layer 372 and the emitter layer 782 may be formed of GaAs, while the window layer 784 is formed of $Al_{1-x}GaAs$. In certain embodiments, the PV cell 310 further includes a p+ GaAs capping layer 386 formed on the window layer 784. Generally, the bandgaps of the active layers of the PV cell 310 are matched closely with the bandgaps of the active layers of the light sources 210 for optimal energy transfer therebetween. Although exemplary embodiments of the PV cell 310 are described with reference to FIG. 3B, those skilled in the art will understand that the PV cell 310 may be optimized by tailoring the composition and structure of the various components or layers thereof.

Figure 4A:
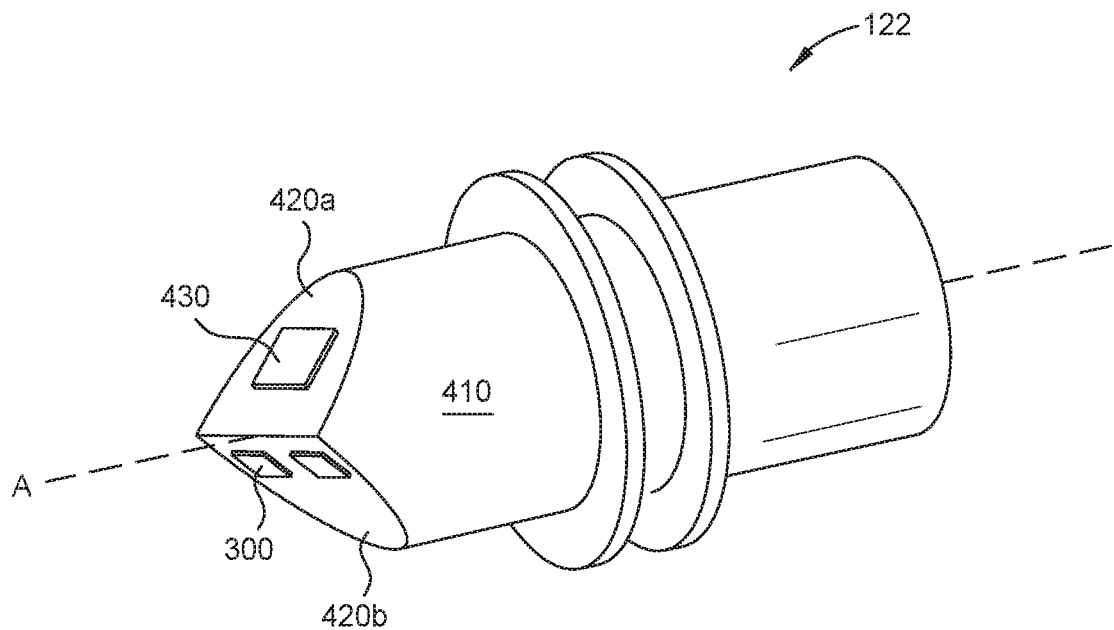
FIGS. 4A-4B illustrate perspective views of the hearing aid of FIG. 1.
Figure 4B:
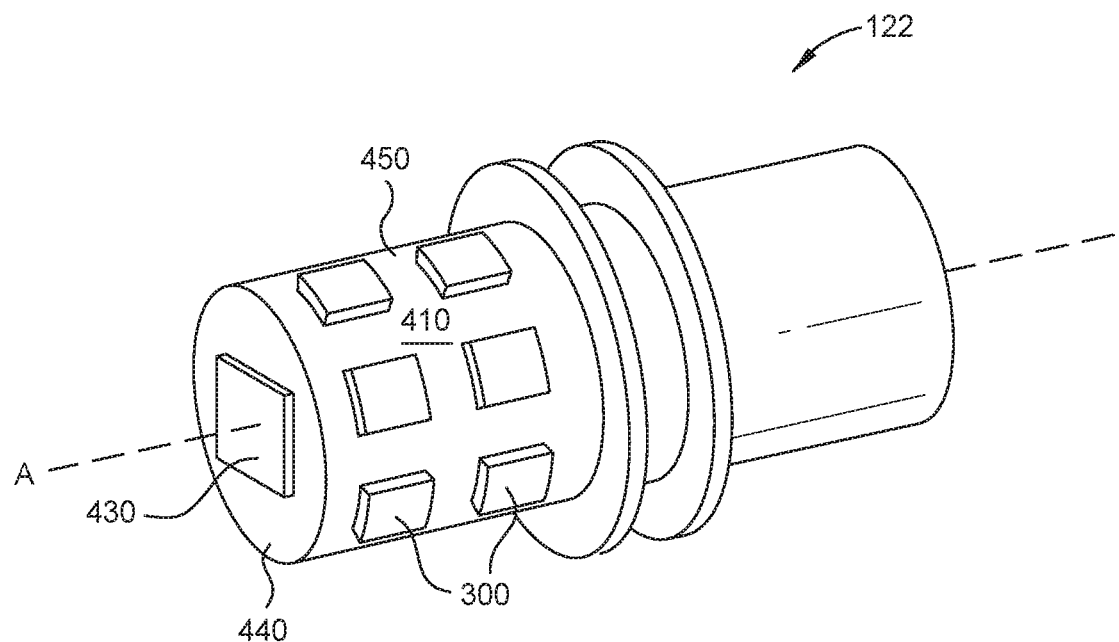

As described above, the PV assembly 300 is generally disposed on a proximal portion of the hearing aid 122 within the ear canal and in an arrangement that avoids interference with the sound detection and amplification functions of the hearing aid 122. FIGS. 4A and 4B illustrate exemplary arrangements of PV assemblies 300 on the hearing aid 122 in accordance with embodiments of the present disclosure. In the embodiment depicted in FIG. 4A, the hearing aid 122 includes a proximal end 410 comprised of at least two oblique and converging surfaces 420a and 420b disposed at angles relative to a major axis A of the hearing aid 122, thus forming a wedge-like shape. In certain embodiments, the oblique surfaces 420a and 420b may be disposed at substantially equal angles relative to the major axis A. In certain other embodiments, the oblique surfaces 420a and 420b may be disposed at substantially different angles relative to the major axis A. Generally, a microphone 430 or other sound detecting device is disposed on the first oblique surface 420a, while one or more PV assemblies 300 are disposed on the second oblique surface 420b. Due to the sloped nature of the oblique surfaces 420a and 420b, both the microphone 430 and the PV assemblies 300 may be aligned to receive direct and indirect (e.g., reflected) acoustic and light energy from the ear canal.

In the alternative embodiment depicted in FIG. 4B, the proximal end 410 of the hearing aid 122 is substantially cylindrical in shape and has a proximal face 440 substantially perpendicular to the major axis A of the hearing aid 122. Either the microphone 430 or the one or more PV assemblies 300 may be disposed on the proximal face 440 (microphone 430 is shown in FIG. 4b), while the other is disposed along the circumferential surface 450 about the hearing aid 122. Thus, either the microphone 430 or the PV assemblies 300 may receive direct acoustic or light energy, while the other receives indirect acoustic or light energy reflected by the surfaces of the ear canal. As previously described, the one or more PV cells 310 of the PV assemblies 300 may absorb light energy emitted by charging device 142 that is reflected off the skin within the ear canal, such as light having a wavelength of about 800 nm.

In addition to transmitting light energy, the charging device 142 may further be configured to wirelessly transmit one or more types of communication signals to the hearing aid 122 for wireless communication between the charging device 142 and the hearing aid 122. In certain embodiments, the hearing aid 122 may be configured to send a modulated signal to the hearing aid 122 for relaying desired commands thereto. Examples of commands that may be communicated between the charging device 142 and the hearing aid 122 include commands to power on and power off the hearing aid 122, or increase and lower the volume thereof.

Aural Inserts and External Support Devices

The present disclosure further contemplates the charging device 142 comprising an aural insert or external support device for securing the light source assembly 200 within or near the ear canal. Generally, during recharging of the hearing aid 122, it is desired that the light source assembly 200 (and thus, the one or more light sources 210) be secured in close proximity to and oriented towards the one or more PV assemblies 300 of the hearing aid 122.

Figure 5A:
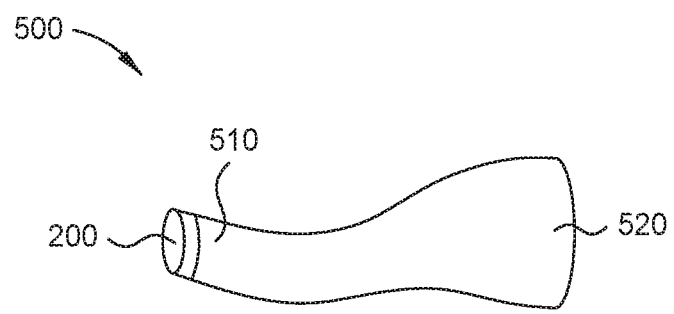
FIGS. 5A-5B illustrate an aural insert for the wireless charging device of FIG. 1.
Figure 5B:
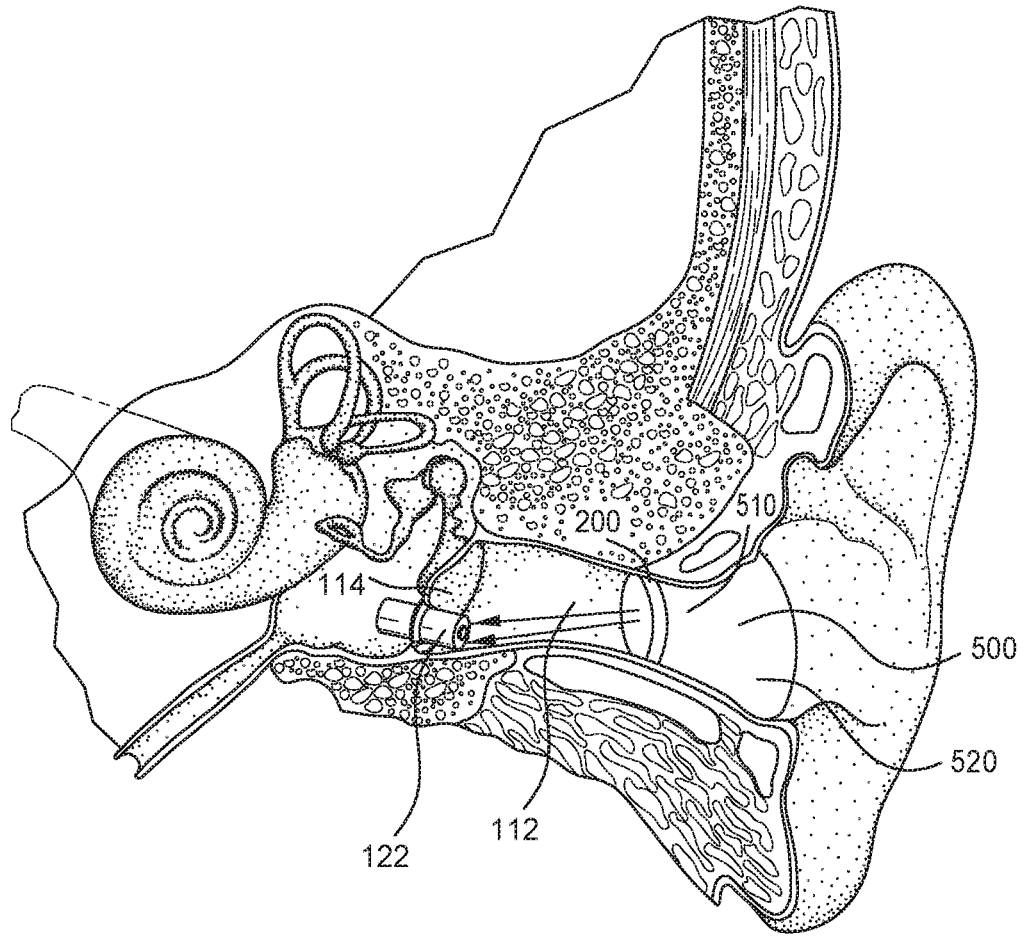

FIGS. 5A-5B illustrate an exemplary aural insert 500 for positioning the light source assembly 200 near the tympanic membrane 114 to provide a direct, clear line of site from the light source assembly 200 to the hearing aid 122. In certain embodiments, the light source assembly 200 is coupled to a distal end 510 of the aural insert 500 which is inserted into the user's ear canal 112, while a proximal end 520 is configured to rest on the concha bowl, the intertragic notch, behind the tragus, or about the entrance of the ear canal 112. In certain embodiments, the proximal end 520 further provides a port for connection to a power source to charge the charging device 142. The distal end 510 is shaped to fit within and traverse at least a portion of the user's ear canal 112, such as between about ½ and about ⅔ of the length of the ear canal 112, to ensure that light from the light source assembly 200 is not impeded by anatomical features or tortuosity of the ear canal 112. Furthermore, the aural insert 500 may have a channel formed through a length thereof (e.g., from a proximal to distal end of the aural insert 500) so as to not impede hearing of the user while wearing the aural insert 500.

In certain embodiments, the aural insert 500 is custom-profiled via ear impression or 3D imaging to match the shape of a specific user's ear canal 112, thus enabling a custom and secure fit. In such embodiments, the aural insert 500 may be formed of relatively rigid materials, such as acrylates and/or methacrylates. In certain other embodiments, the aural insert 500 has a universal fit and does not require custom profiling, and is thus formed of suitable malleable or flexible materials to conform to the tortuosity and length of the ear canal 112. Examples of suitable malleable materials include polymers such as rubber and silicone, polyurethane, foam, advanced plastics, and the like. In certain examples, the aural insert 500 may be compressed by the user prior to insertion within the ear canal 112, after which the aural insert 500 may decompress to fill the ear canal 112. In certain embodiments, the aural insert 500 is formed of an optically transparent or translucent material to enable transmission of light therethrough.

In addition to the aural insert 500, the present disclosure also contemplates the charging device 142 comprising other types of external support devices for securing or mounting the light source assembly 200 within or near the ear canal. The external support devices are generally disposed near the ear canal, over the ear, around the ear, or in the vicinity of the user's head. Exemplary external support devices include ear buds, earmuffs, over-the-ear clips, glasses stem clips, headbands, and devices in or around the vicinity of the user's head that can be placed near the ear canal, over the ear, around the ear, or in the vicinity of the user's head to enable interaction between the light source assembly 200 and the PV assemblies 300 of the hearing aid 122.

Figure 6:
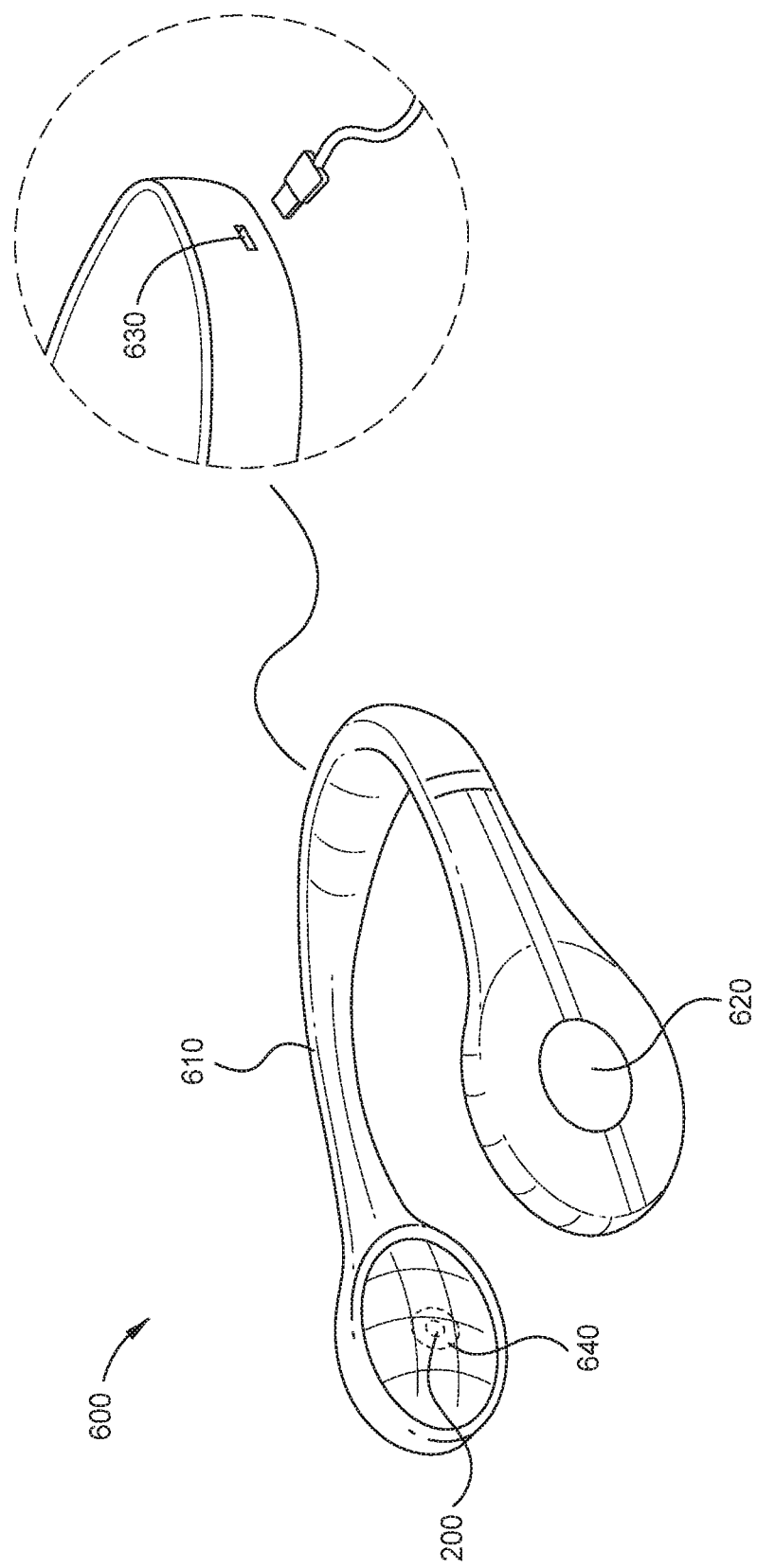
FIG. 6 illustrates an external support device for the wireless charging device of FIG. 1.

FIG. 6 illustrates one such external support device in the form of earmuffs 600 for securing and stabilizing a light source assembly 200 in or near the ear canal of a user. As shown, the earmuffs 600 include a headband 610 coupled to two ear cups 620 at opposing ends thereof, wherein at least one ear cup 620 has a light source assembly 200 disposed therein. When worn, the ear cups 620 are placed over the external ear (e.g., over the concha bowl) of the user, thus positioning the light source assembly 200 near the entrance of the user's ear canal for recharging of the hearing aid 122. In certain embodiments, the light source assembly 200 may be disposed within a removable pod 640 for easy insertion and removal from the earmuffs 600. The earmuffs 600 also include a USB port 630 for USB charging of the earmuffs 600.

FIGS. 7A-7D illustrate another exemplary external support device in the form of a headband 700. The headband 700 includes at least one pouch 710 disposed on an internal or external side thereof for securing a light source assembly 200 near a user's ear canal when worn over the external ear of the user. Like with the earmuffs 600, the pouch 710 may be configured to receive the light source assembly 200 within a pod 640 for easy insertion and removal therefrom. The headband 700 is generally formed of any suitable materials, including fabrics or polymeric materials such as silicone for user comfort. In certain embodiments, the headband 700 is a standalone device. In certain other embodiments, the headband 700 is further integrated with another piece of headwear, such as a hat or skullcap 720, to be worn by the user during use of the charging device 142.

Figure 8C:
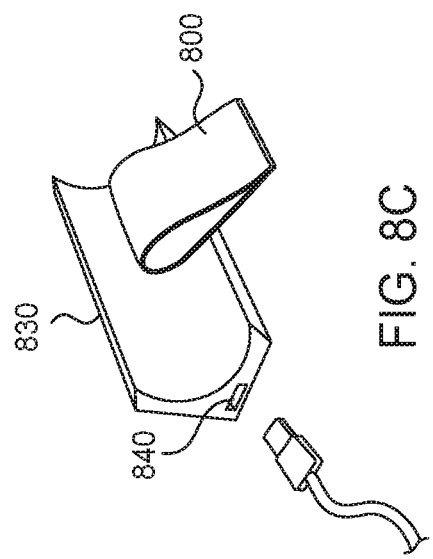
FIGS. 8A-8C illustrate an external support device for the wireless charging device of FIG. 1.
Figure 8B:
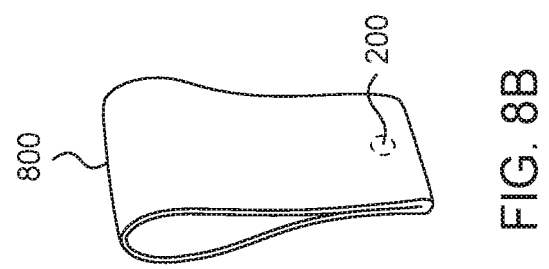
Figure 8A:
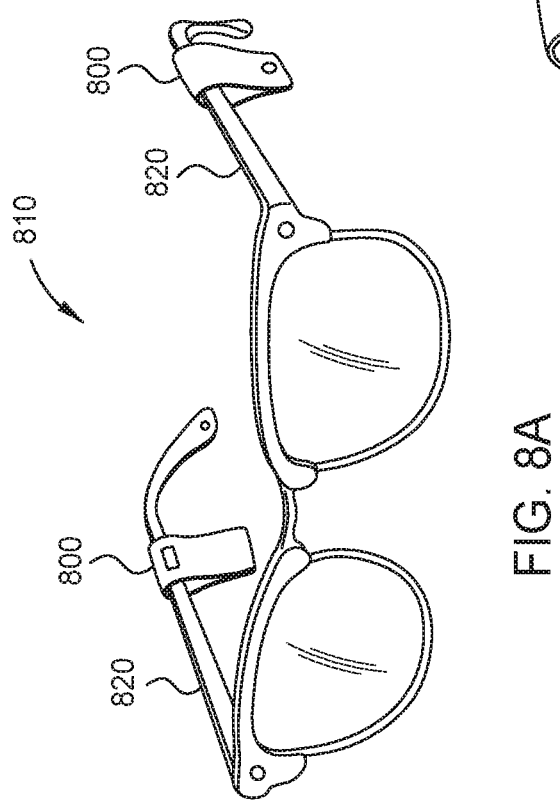

FIGS. 8A-8C illustrate exemplary eyeglass stem clips 800 for securing the light source assembly 200 in or near the ear canal of a user. As depicted, the eyeglass stem clips 800 may slide over or attach to (e.g., clip to) the stems 820 of a pair of eyeglasses 810 during use thereof. When not being utilized, the eyeglass stem clips 800 may be removed from the eyeglasses 810 and coupled with a charging dock 830 having a USB port 840 for charging/recharging thereof. The eyeglass stem clips 800 are generally formed of any suitable materials, including polymeric materials such as silicone.

Figure 9:
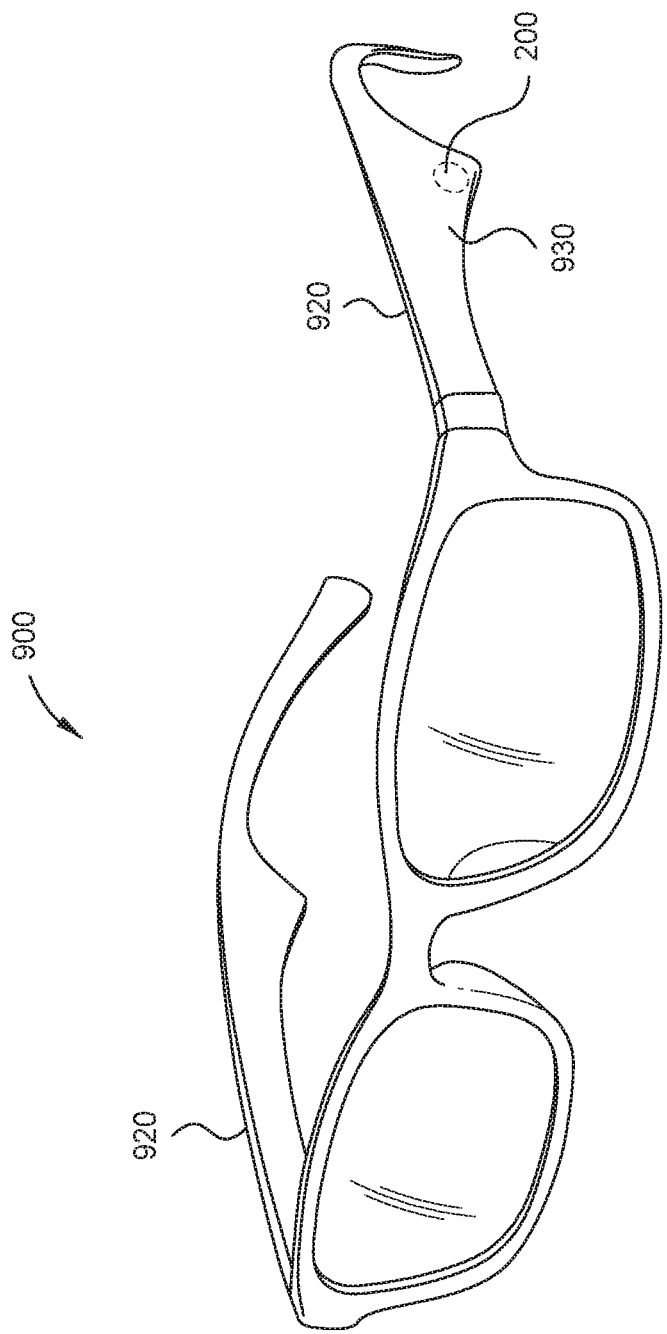
FIG. 9 illustrates an external support device for the wireless charging device of FIG. 1.

As an alternative to the eyeglass stem clips 800, FIG. 9 illustrates an exemplary eyeglass frame 900 having a light source assembly 200 integrated therewith. As shown, one or both stems 920 of the eyeglass frame 900 has a protrusion 930 extending therefrom and configured to receive a light source assembly 200. When worn, the protrusion 930 extends over the ear and positions the light source assembly 200 in or near the user's ear canal. Like the earmuffs 600, the eyeglass frame 900 may have a USB port for USB charging/recharging of the eyeglass frame 900 when not in use.

Figure 10B:
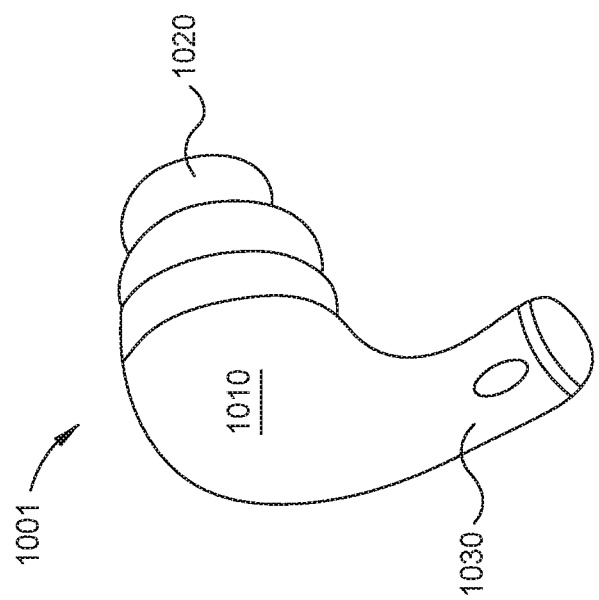
FIGS. 10A-10B illustrate external support devices for the wireless charging device of FIG. 1.
Figure 10A:
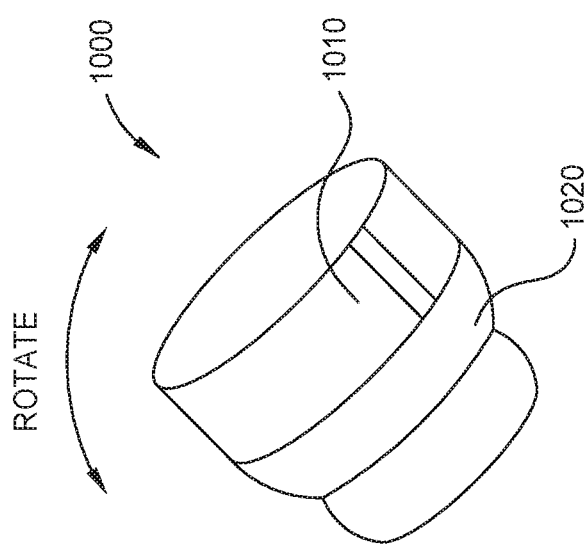

FIGS. 10A-10B illustrate exemplary concha devices 1000 and 1001 for positioning the light source assembly 200 in or near the ear canal while substantially resting within the concha bowl (e.g., cavum concha) of the user's ear. Generally, the concha devices 1000 and 1001 comprise a base 1010 coupled to a fitting 1020. Concha device 1001 further includes a stem 1030 for easier handling by a user. The base 1010 houses the light source assembly 200 and any corresponding circuitry and rests external to the ear canal during use, while the fitting 1020 is configured to fit into the ear canal and secure (e.g., anchor) the device to the user's ear. Similar to the aural insert 500, the fitting 1020 is formed of any suitable malleable or flexible material to conform to the tortuosity of the ear canal, including polymers such as rubber and silicone, polyurethane, foam, and/or advanced plastics. Accordingly, the fitting 1020 may be compressed by the user prior to insertion within the ear canal, after which the fitting 1020 may decompress to fill the ear canal. In certain embodiments, the material of the fitting 1020 is optically transparent or translucent to enable transmission of light therethrough. In certain embodiments, the fitting 1020 has a cavity or channel formed therein to enable transmission of light from the light source assembly 200 to the hearing aid 122.

Figure 11:
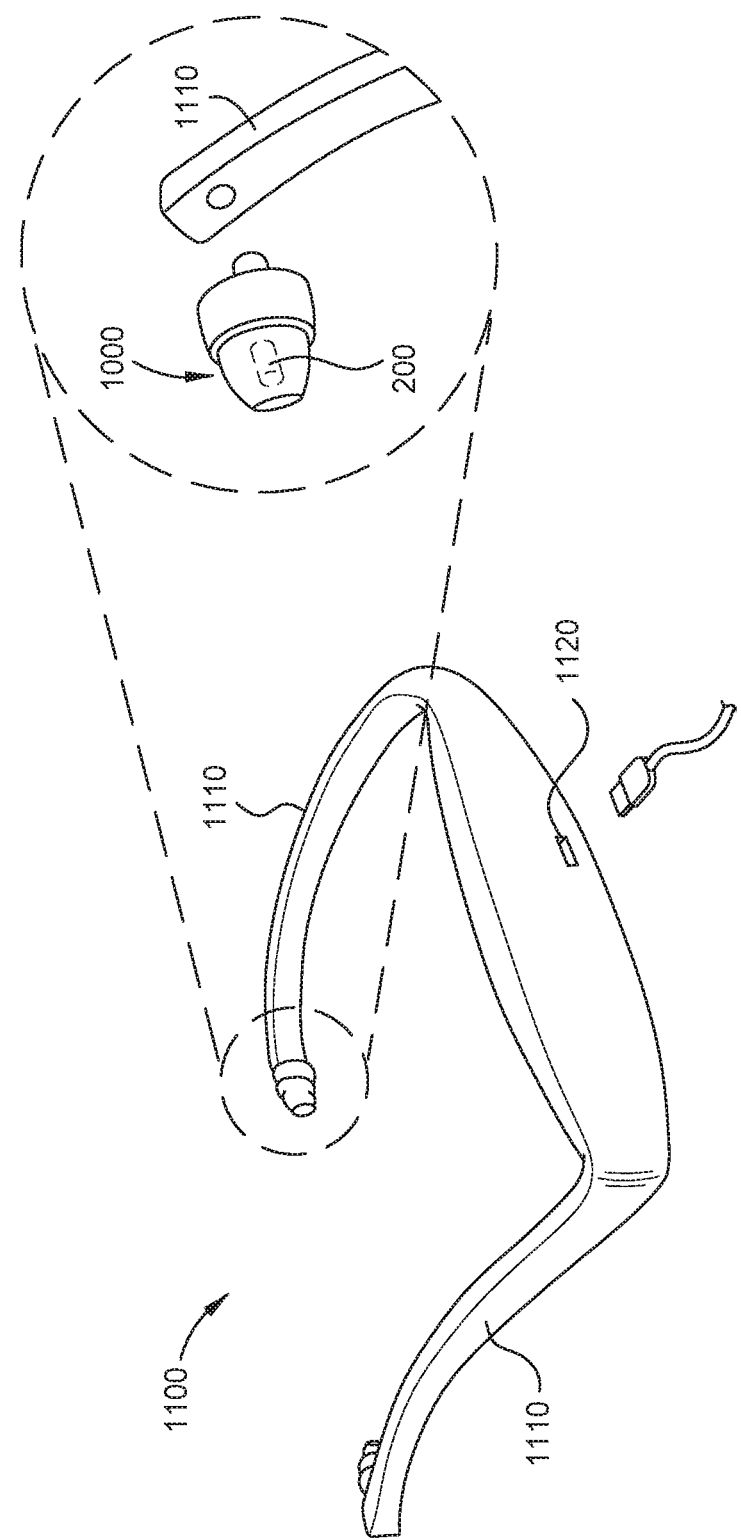
FIG. 11 illustrates an external support device for the wireless charging device of FIG. 1.
Figures 12A, 12B:
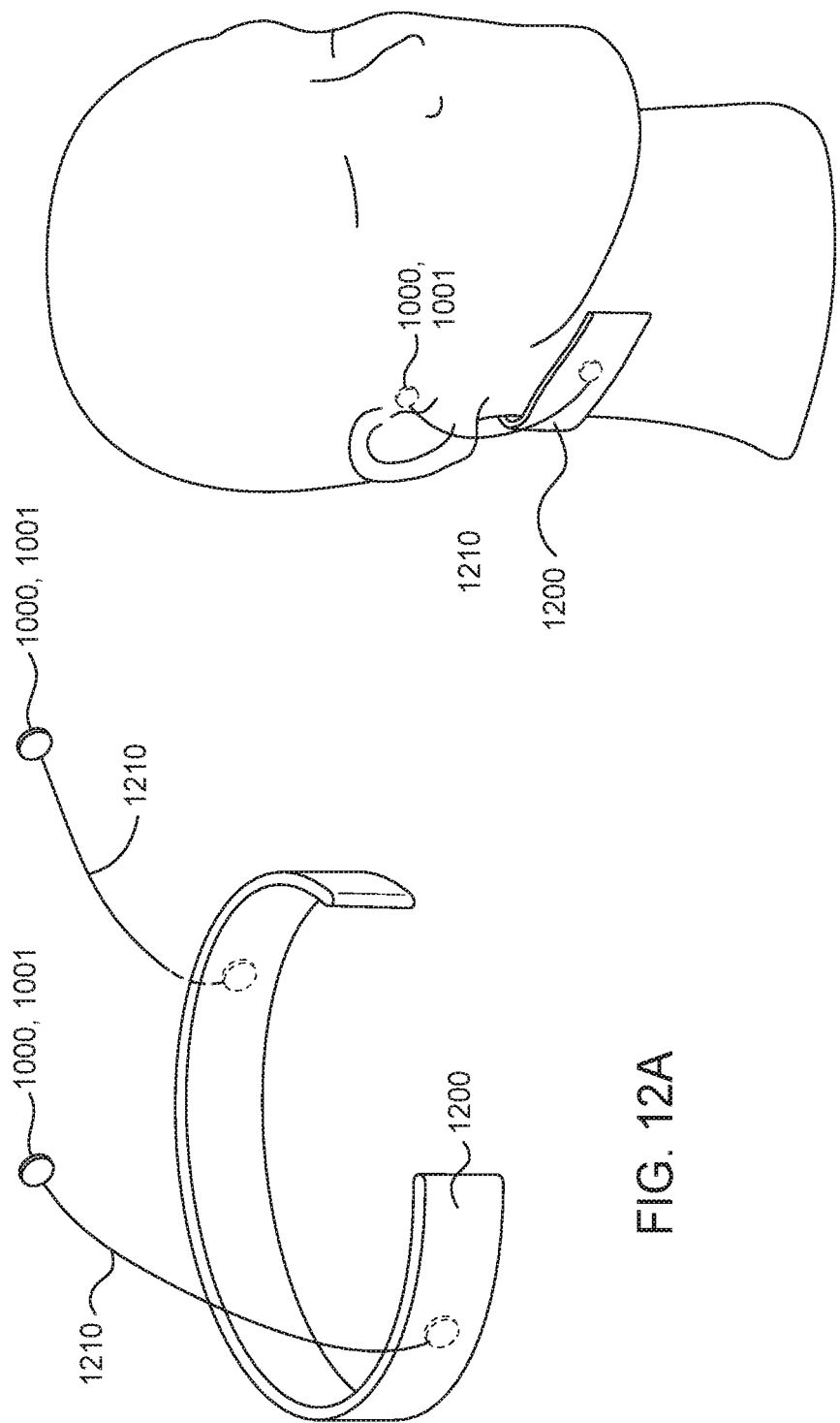
FIGS. 12A-12B illustrate an external support device for the wireless charging device of FIG. 1.
Figure 13B:
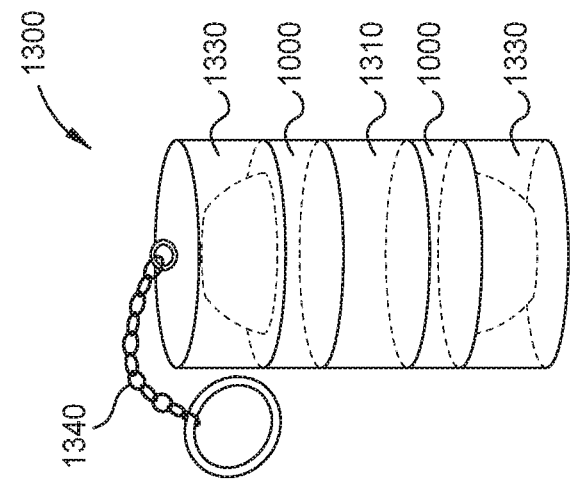
FIGS. 13A-13B illustrate an accessory for an external support device of the wireless charging device of FIG. 1.
Figure 13A:
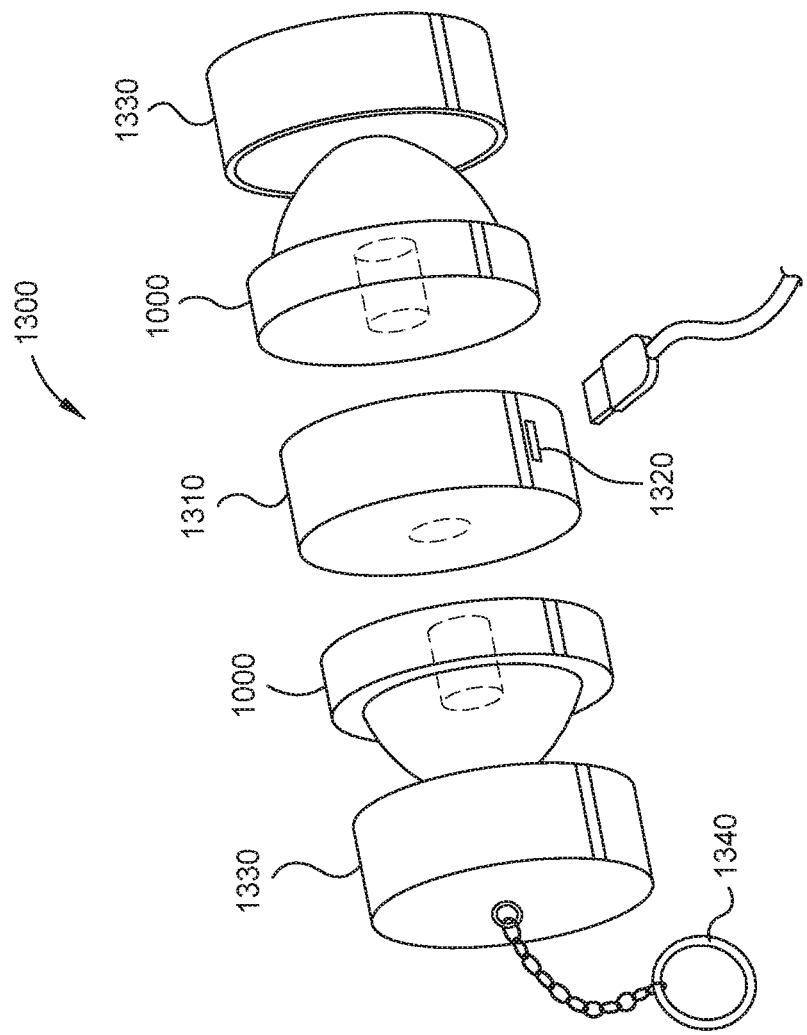
Figure 15A:
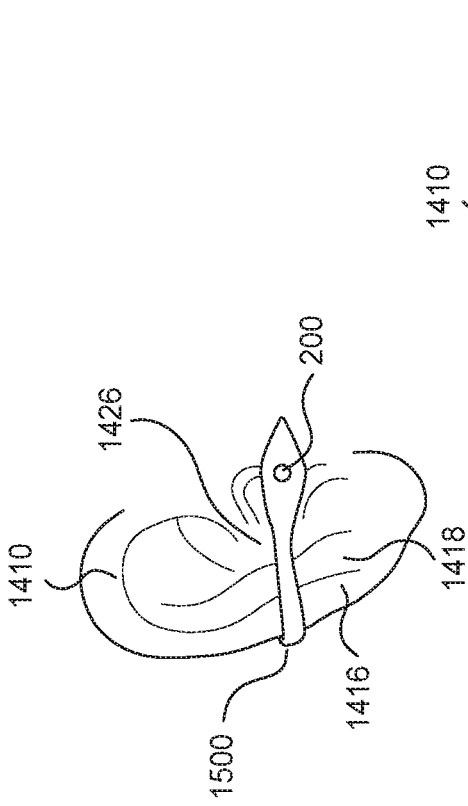
FIGS. 15A-15B illustrate an external support device for the wireless charging device of FIG. 1.
Figure 15B:
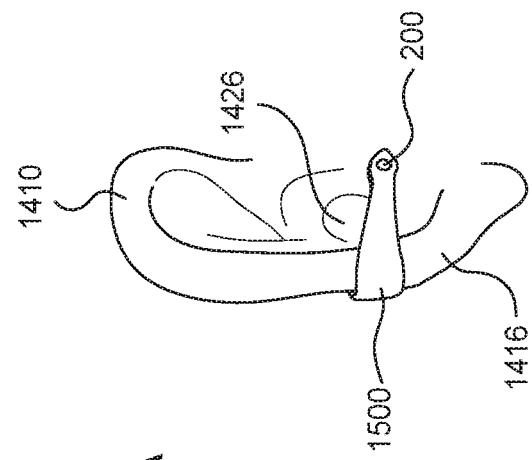
Figure 14A:
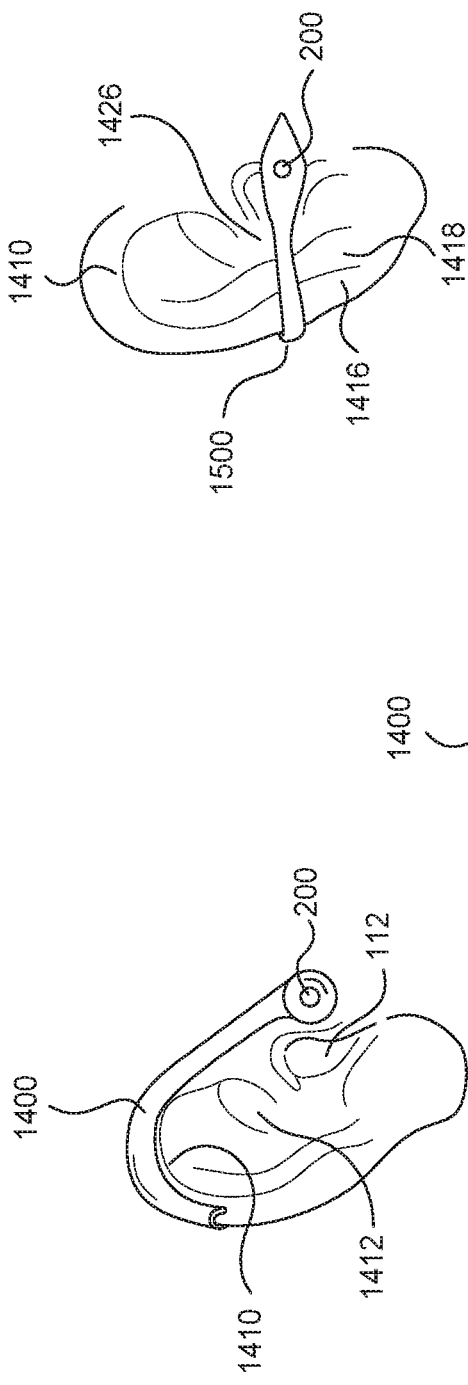
FIGS. 14A-14B illustrate an external support device for the wireless charging device of FIG. 1.
Figure 14B:
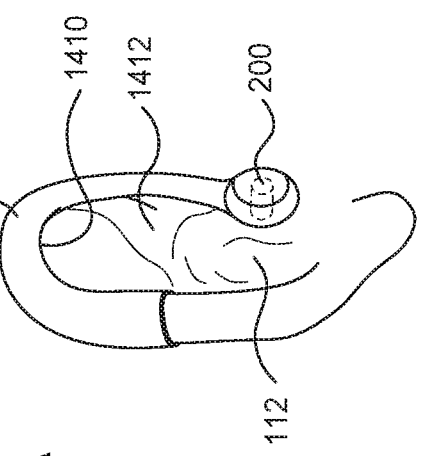

FIGS. 11, 12A-12B, and 13A-13B illustrate additional components that may be utilized in combination with the concha devices 1000 and 1001 described above. In FIG. 11, the concha device 1000 removably couples to stems 1110 of a headband 1100, which may further include a USB port 1120 for USB charging/recharging of the headband 1100 and/or concha device 1000. The headband 1100 provides additional support for securing the concha device 1000 within the concha bowl during use thereof. As depicted in FIGS. 12A-12B, either of the concha devices 1000 or 1001 may further be secured to a neckband 1200 by cables 1210. The neckband 1200 is shaped to be supported upon a user's neck by tension, and provides an anchoring point for the concha devices 1000 and 1001 to prevent a user from dropping or losing the devices. FIGS. 13A-13B depict a portable and modular charging unit 1300 for the concha device 1000. The charging unit 1300 includes a charging base 1310 having USB port 1320 for USB charging/recharging of one or more concha devices 1000. During use, the concha devices 1000 may anchor to opposing sides of the charging base 1310 by any suitable means, including mechanical or magnetic mechanisms. In certain embodiments, the charging unit 1300 also includes one or more caps 1330 that attach to the charging base 1310 or the concha devices 1000 themselves and cover the concha devices 1000 when anchored to the base 1310. In certain embodiments, the one or more caps 1330 are further coupled to a keychain 1340 or other tethering device for attachment to other devices.

FIGS. 14A-14B, 15A-15B, and 16A-16B illustrate further examples of external support devices for securing the light source assembly 200 in or near the ear canal of a user. In FIGS. 14A-14B, 15A-15B, and 16A-16B, the light source assembly 200 is coupled to distal ends of ear cuffs 1400, 1500, and 1600, respectively, which encircle or wrap around various features of the external ear for support. For example, the ear cuff 1400 encircles the upper helix 1410 of the ear and extends down past the crus 1412 of the helix to the entrance of the ear canal 112, where it secures the light source assembly 200. The ear cuff 1500, on the other hand, wraps around a portion of the lower helix 1416 and extends therefrom to the entrance of the ear canal 1214, thus extending past the lower antihelix 1418 and the concha bowl 1426. Alternatively, the ear cuff 1600 includes two arms 1610 which wrap around a portion of the upper helix 1410 and a portion of the lower helix 1416 and converge over the concha bowl 1426 in a direction towards the ear canal 112 where the light source assembly 200 may be attached.

FIGS. 17A-17B illustrate yet another external support device in the form of a triangular earpiece 1700. The triangular earpiece 1700 includes three vertices 1710, 1720, and 1730 that may be inserted within the folds of the upper helix 1410, the lower helix 1416, and behind the tragus 1420 of the user's ear, thus enabling the triangular earpiece 1700 to be completely supported therebetween by tension. As depicted, the light source assembly 200 is disposed at the vertex 1730 supported behind the tragus 1420, thereby positioning the light source assembly 200 in or near the entrance of the ear canal 112.

In FIGS. 18A-18B, the light source assembly 200 is coupled to an ear bracelet 1800 that may encircle a medial portion of the auricle 1422, or where the external ear attaches to the user's head. During use, the portion of the ear bracelet 1800 supporting the light source assembly 200 may be pulled around the tragus 1420 such that the ear bracelet 1800 is secured in place by tension. In FIGS. 19A-19B, the light source assembly 200 is coupled to a backside of a piercing 1900 through the tragus 1420, such as an earring stud. Accordingly, the piercing 1900 provides a secure attachment point for the light source assembly 200 near the ear canal 112 while occupying minimal space on the user's ear.

FIGS. 20A-20B illustrate another exemplary external support device in the form of an ear cap 2000 that may function similar to a sleeve. The ear cap 2000 is generally configured to slide over a top portion of the auricle 1422 such that the light source assembly 200, which may be supported within a pouch thereof, is positioned near the ear canal 112. The ear cap 2000 is formed of any suitable malleable materials, including fabrics or silicone.

In FIGS. 21A-21B, the light source assembly is attached to an S-shaped ear wrap 2100. A top portion of the s-shaped ear wrap 2100 hooks around a top portion of the auricle 1422 and crosses over to extend past the tragus 1420, where the light source assembly 200 is attached and oriented towards the ear canal 112. Similar to the top portion thereof, a bottom portion of the s-shaped ear wrap 2100 hooks around the bottom portion of the auricle 1422, such as the lobule 1424, to provide further support and stability to the s-shaped ear wrap 2100.

Figure 22B:
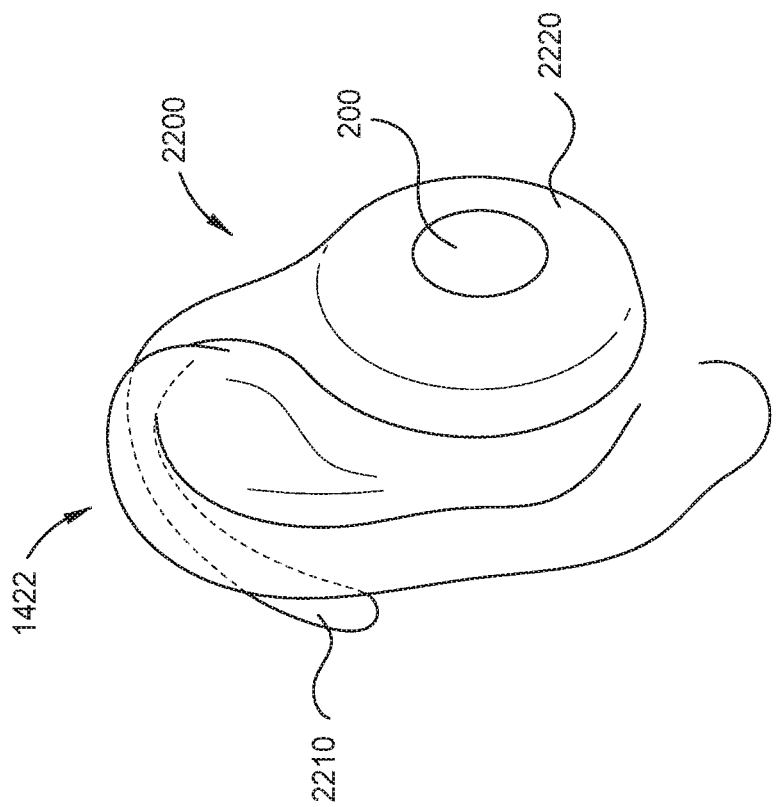
FIGS. 22A-22B illustrate an external support device for the wireless charging device of FIG. 1.
Figure 22A:
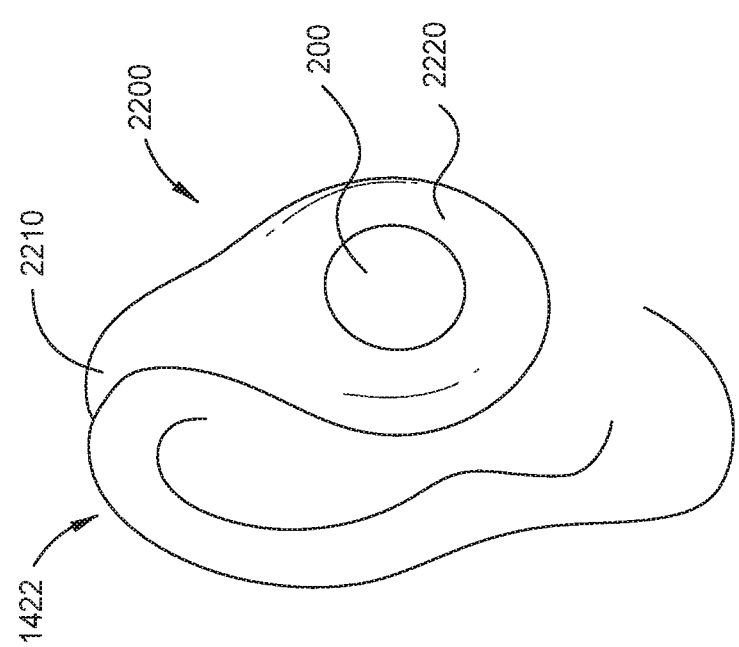

FIGS. 22A-22B illustrate another exemplary external support device in the form of an ear hook assembly 2200. The ear hook assembly 2200 generally includes an ear hook 2210 extending from a base 2220 that houses or couples the light source assembly 200 thereto. In certain embodiments, the base 222 is an earcup (e.g., earmuff cup) that rests over a portion of the ear including the entrance of the ear canal 112, similar to the earmuffs 600 described above. In certain other embodiments, the base 2220 is a concha device that rests within the concha bowl 1426, similar to the concha device 1000. During operation, the ear hook 2210 slides over the top portion of the auricle 1422 and rests on a backside of the ear while the base 2220 is positioned over the entrance of the ear canal 112 to stabilize the light source assembly 200 in or near the ear canal 112.

CONCLUSION

In summary, embodiments of the present disclosure provide improved charging and recharging systems for hearing aids implanted within or near the ear canal, such as those implanted through the tympanic membrane. The disclosed systems utilize photovoltaic devices that efficiently generate power for implants from artificially-produced light transmitted across the ear canal, thus eliminating the need for external implant power supplies or charging components. Moreover, the disclosed systems provide compact and wireless light emitting devices that may be worn in or near the ear canal during recharging, thus enabling a user engage in other activities without significant impedance thereof. Accordingly, the disclosed systems enable the implantation of hearings aids that are more compact, more comfortable, and less cosmetically noticeable.

While the foregoing is directed to embodiments of the present disclosure, other and further embodiments of the disclosure may be devised without departing from the basic scope thereof, and the scope thereof is determined by the claims that follow.

What is claimed is:

1. A charging system for a hearing aid implant, comprising:
   one or more photovoltaic (PV) cells disposed on a proximal end of the hearing aid implant, the hearing aid implant disposed through a tympanic membrane of an ear; and
   one or more light sources configured to be inserted in or near an entrance of an ear canal of the ear, the one or more light sources emitting a light energy receivable by the one or more PV cells to charge the hearing aid implant.

2. The charging system of claim 1, wherein the one or more light sources emit a light energy having a wavelength in a range from about 400 nm to about 870 nm, the wavelength further corresponding to a wavelength range of high reflectivity by one or more surfaces of the ear canal.

3. The charging system of claim 2, wherein the one or more light sources comprise a narrow wavelength light source emitting a light energy having a wavelength of about 800 nm.

4. The charging system of claim 2, wherein the one or more light sources have a peak wavelength about 50 nm less than a peak absorptivity of the one or more PV cells.

5. The charging system of claim 1, wherein the one or more light sources comprise a light emitting diode (LED).

6. The charging system of claim 5, wherein the one or more light sources comprise a high spectral purity, high efficiency resonant cavity LED.

7. The charging system of claim 1, wherein the one or more light sources are disposed within a light source assembly, the light source assembly comprising a secondary optic to focus light energy emitted from the one or more light sources.

8. The charging system of claim 7, wherein the secondary optic is configured to focus light on a focal plane between about 1 mm and about 30 mm from the light source assembly.

9. The charging system of claim 1, wherein the one or more light sources are disposed on a distal end of a support device configured to at least partially rest external to the ear canal.

10. The charging system of claim 9, wherein the support device is an aural insert configured to traverse between about 1/5 and about 2/3 of a length of the ear canal during operation, the aural insert comprising a channel formed from the distal end to a proximal end thereof so as not to impede hearing of a user.

11. The charging system of claim 9, wherein the support device comprises earmuffs, the earmuffs further comprising:
   a headband; and
   one or more ear cups attached to opposing ends of the headband, wherein the one or more light sources are disposed within at least one of the one or more ear cups and are configured to be positioned in or near the entrance of the ear canal during operation.

12. The charging system of claim 9, wherein the support device comprises a concha device, the concha device further comprising:
   a base for housing the one or more light sources, the base configured to rest external to the ear canal during operation; and
   a malleable fitting configured to fit into the ear canal and secure the support device to the ear.

13. The charging system of claim 12, wherein the concha device is removably coupled to a headband or neckband.

14. The charging system of claim 9, wherein the support device comprises:
   an ear cup for housing the one or more light sources, wherein the one or more light sources are disposed within the ear cup and are configured to be positioned in or near the entrance of the ear canal during operation; and
   an ear hook coupled to the ear cup, the ear hook configured to slide over a top portion of an auricle of the ear and rest on a backside of the ear while supporting the ear cup over the entrance of the ear canal.

15. The charging system of claim 9, wherein the support device is further configured to wirelessly communicate with the hearing aid implant and transfer one or more wireless command signals thereto.

16. A charging system for a hearing aid implant, comprising:
   one or more photovoltaic (PV) cells disposed on a proximal end of the hearing aid implant, the hearing aid implant disposed through a tympanic membrane of an ear; and
   a charging device configured to be inserted in or near an entrance of an ear canal of the ear, the charging device comprising one or more light sources emitting a light energy receivable by the one or more PV cells of the hearing aid implant and having a wavelength corresponding to a wavelength range of high reflectivity by one or more surfaces of the ear canal, wherein the one or more PV cells convert the light energy into stored electricity to power the hearing aid implant.

17. The charging system of claim 16, wherein the charging device is further configured to wirelessly communicate with the hearing aid and transfer one or more wireless command signals thereto.

18. The charging system of claim 16, wherein the one or more light sources comprise a high spectral purity, high efficiency resonant cavity light emitting diode (LED) emitting a light energy having a wavelength in a range from about 400 nm to about 870 nm.

19. The charging system of claim 18, wherein the one or more light sources have a peak wavelength about 50 nm less than a peak absorptivity of the one or more PV cells.

20. A charging system for a hearing aid implant, comprising:
   one or more photovoltaic (PV) cells disposed on a proximal end of the hearing aid implant, the hearing aid implant disposed through a tympanic membrane of an ear; and
   a charging device configured to be inserted in or near an entrance of an ear canal of the ear, the charging device comprising:
      one or more high spectral purity, high efficiency resonant cavity light emitting diodes (LEDs) for emitting a light energy having a wavelength corresponding to a wavelength range of high reflectivity by one or more surfaces of the ear canal, wherein the one or more PV cells are configured to absorb the light energy emitted directly from the one or more LEDs and light energy reflected by the one or more surfaces of the ear canal and convert the light energy into stored electricity to power the implanted hearing aid; and
      a support device coupled to the one or more LEDs and configured to at least partially rest external to the ear canal and secure the charging device to the ear.

* * * * *